United States Patent [19]

Mohler et al.

[11] Patent Number: 4,977,523

[45] Date of Patent: Dec. 11, 1990

[54] APPARATUS FOR THE MEASUREMENT OF SNOW QUALITY

[75] Inventors: Robert D. Mohler, Fairport; James C. Liao, Webster, both of N.Y.

[73] Assignee: Eastman Kodak Company, Rochester, N.Y.

[21] Appl. No.: 294,525

[22] Filed: Jan. 6, 1989

[51] Int. Cl.$^5$ ............................................. G01N 1/14
[52] U.S. Cl. ...................................... 364/550; 73/76; 73/170 R; 374/31
[58] Field of Search ................... 364/550, 551.01, 557; 73/76, 73, 29, 170 R, 171; 374/31, 33, 34, 42

[56] References Cited

U.S. PATENT DOCUMENTS

| | | | |
|---|---|---|---|
| 3,413,838 | 12/1968 | Duddy | 73/29 |
| 3,646,812 | 3/1972 | Ishii | 374/31 |
| 4,499,761 | 2/1985 | Plank et al. | 73/170 R |
| 4,753,889 | 6/1988 | Collins | 73/76 X |
| 4,769,593 | 9/1988 | Reed et al. | 374/42 X |
| 4,787,052 | 11/1988 | Yamaguchi et al. | 364/550 |
| 4,799,379 | 1/1989 | Suga | 73/76 |
| 4,832,503 | 5/1989 | Dowling et al. | 374/42 |
| 4,838,705 | 6/1989 | Byers, Jr. et al. | 73/76 X |
| 4,849,988 | 7/1989 | Chien | 374/42 |

Primary Examiner—Joseph L. Dixon
Attorney, Agent, or Firm—J. Jeffrey Hawley

[57] ABSTRACT

There are disclosed a method and an apparatus for the measurement of the ice content of snow. Ice content is directly related to the quality of the snow. The method comprises the steps of measuring the weight of ice in the sample by:

(1) placing a sample of the snow to be measured in a sample chamber;
(2) heating said sample chamber and measuring the heat supplied while measuring its temperature; and
(3) calculating the weight of the ice in the sample from the measurements in step (2), and then dividing the weight of the ice in the sample by the total weight of the sample to obtain a value for the snow quality. There is also provided an apparatus for carrying out the described method. The apparatus includes an insulated sample chamber including provision for heating and temperature sensing. The sample chamber is detachably connected to a microprocessor based instrument which controls the heating of the chamber and calculates the ice content from the heat supplied and temperature measurements.

4 Claims, 2 Drawing Sheets

APPARATUS FOR THE MEASUREMENT OF SNOW QUALITY

FIELD OF THE INVENTION

The present invention is directed to the measurement of snow quality by measuring the ice content of a sample of the snow.

DESCRIPTION RELATIVE TO THE PRIOR ART

The measurement of snow quality is important for several reasons. For example, in avalanche prevention, it is important to measure the quality of the snow so that appropriate steps can be taken if a dangerous situation develops. However, one of the more important instances where the measurement of snow quality is necessary is in the making of artificial snow.

The making of artificial snow for ski resorts is a large business. Commercial ski resorts spend large sums of money on snow making equipment and the energy to run the snow making operation. It is important therefore, that the operation be as efficient as possible. Even small improvements in the operation can be economically beneficial.

There are several methods for measuring the quality of the snow that is produced in an artificial snow making operation. Among the most common methods is the "snow ball" method. In this method, an experienced operator packs a sample of the snow to be tested in his hands and subjectively evaluates the ball that is produced. For example, if the snow is extremely dry, it will be difficult if not impossible to make a useful snow ball. If the snow is extremely wet, water will run out of the ball. With experience, an operator can grade the snow ball produced into one of six grades.

It will be appreciated that this method is highly subjective and not accurate. It is difficult to detect small changes in snow quality and therefore difficult to optimize the snow making operation.

Another popular method is the so called "black sleeve" method. In this method, the operator allows the freshly made snow to fall on his black sleeve. The snow can then be inspected and brushed off the sleeve. Again, an experienced operator can roughly judge the quality of the snow produced, however, this method is also subjective and inaccurate.

One more scientific method has been recently developed for the measurement of snow quality. In this method, a dielectric probe is placed in the snow and the dielectric constant of the snow is measured. Depending on the water content of the snow, the dielectric constant will vary. Thus, this method has the potential of being much more accurate than the previously described methods. Unfortunately however, the dielectric constant also varies depending on the air content of the snow and the morphology of the ice crystals. It is therefore difficult to get consistent readings.

Thus, there is a continuing need for a simple yet accurate method and apparatus for determining snow quality.

SUMMARY OF THE INVENTION

In accordance with the present invention, snow quality is measured by measuring the ice content of a snow sample. It has been determined that the ice content correlates well with the traditional methods of measuring snow quality such as the snow ball method and the black sleeve method.

Thus, there is provided a method for measuring the ice content of snow, said method comprising the steps of measuring the weight of ice in the sample by:

(1) placing a sample of the snow to be measured in a sample chamber;
(2) heating said sample chamber and measuring the heat supplied while measuring its temperature; and
(3) calculating the weight of the ice in said sample from the measurements in step (2), and then dividing the weight of the ice in the sample by the total weight of the sample to obtain a value for the snow quality.

In accordance with another aspect of the invention there is provided an apparatus that is particularly suited to carrying out the above method. Thus, there is provided an apparatus for measuring the ice content of snow, said apparatus comprising:

(a) an insulated sample chamber for receiving a sample of said snow, said sample chamber including:
  (i) means for heating said chamber and
  (ii) means for measuring the temperature of said chamber; and
(b) computing means detachably connected to said sample chamber including
  (i) means for controlling said means for heating and for measuring the amount of heat supplied to said chamber;
  (ii) means for monitoring said means for measuring temperature; and
  (iii) means for calculating the ice content of said sample from the heat supplied to said chamber and its temperature.

The method and apparatus of the invention provide for the accurate and repeatable measurement of the quality of snow and particularly the amount of ice that is produced in an artificial snow making operation. With the method and apparatus of the invention, the operation can be easily optimized to get the maximum amount of snow from any particular environmental condition.

A particular feature of the apparatus of the invention is that the insulated sample chamber is detachably connected to the remainder of the instrument. In this way, a plurality of inexpensive sample chambers can be provided that can receive samples of snow from a number of remote locations. The sample chambers can then be transported a central site and then connected to the remainder of the instrument. Thus, only one expensive instrument is needed. Further, the instrument is easier to operate and calibrate away from the snow making site.

DETAILED DESCRIPTION OF THE INVENTION

For the present purposes, snow quality is defined as the weight of ice in a sample divided by the total weight of ice and water. Thus, it is necessary to determine the total weight of a sample as well as the weight of the ice in the sample. The weight of the ice in the sample is determined using calorimetry.

If heat is put into a sample containing ice, the temperature will rise until the sample reaches the melting temperature of the ice. The equilibrium temperature will then remain the same as the heat energy is taken up as the latent heat of fusion until all of the ice melts. The temperature will then begin to rise again. Since the latent heat of fusion of water is known, the weight of the ice can be calculated from the amount of heat that is put into the sample during the constant temperature period.

The total weight of the sample can be determined in two ways. The weight of the sample can be determined directly by weighing the sample on a balance. This is the preferred method. In the alternative, the sample can be continued to be heated after all of the ice melts. The rate of increase in temperature is related to the weight of the sample by the heat capacity of water.

Figure 1:
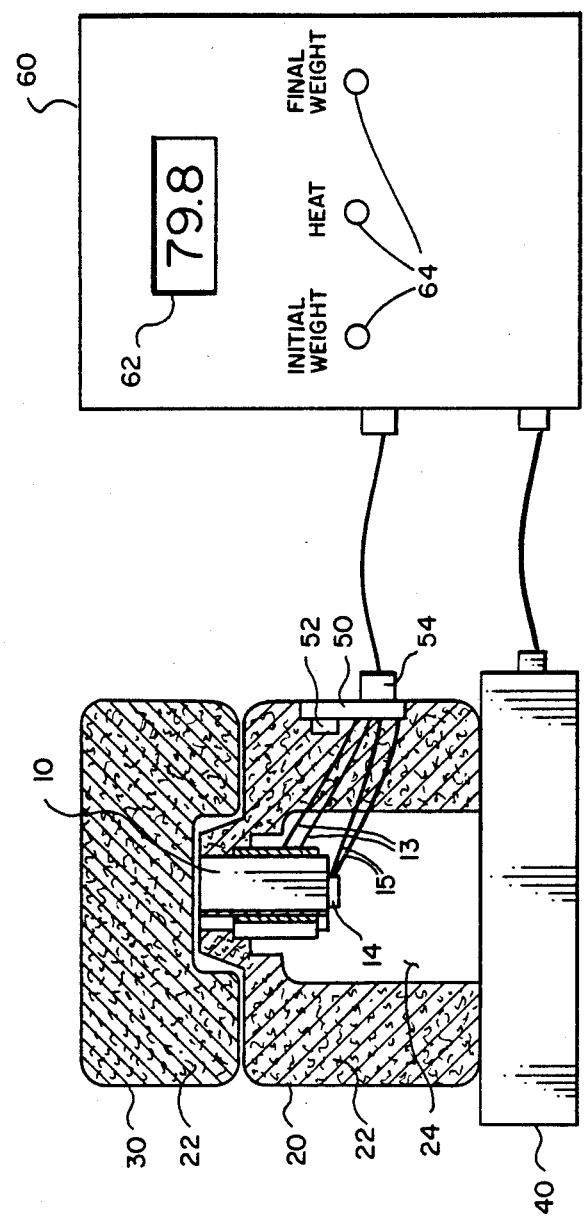
FIG. 1 is a schematic representation of the apparatus according to the invention.

A preferred apparatus of the invention is illustrated in FIG. 1. The sample chamber 10 and the surrounding structure is shown in cross section. The sample chamber 10 is preferably a metal cup. To increase the surface to volume ratio, the metal cup is preferably triangular in shape as viewed from the top. The sample chamber is wrapped with a heater tape shown in cross section at 12. The heater type 13 is connected to circuit board 50 by wires 13. A temperature sensor 14 is attached to the bottom of the cup. The temperature sensor 14 is connected to circuit board 50 by wires 15.

The sample cup 10 is located in container 20 which is at least partially filled with insulation 22. The container 20 has a matching lid 30 also containing insulation 22.

As is shown, the container 20 is preferably only partially filled with insulation 22. It was found that it was not desirable for the insulation to contact the sample chamber over its whole surface. During the calibration of the sample chamber, the chamber must be brought to the desired temperature quickly. Since the heat capacity of the insulation is higher than air, if the insulation contacts the chamber, it might take longer for the chamber to reach the desired starting temperature. Further, it is difficult to achieve uniform contact of the insulation with the chamber. As a result of the air space 24 shown in FIG. 1, these problems are reduced and the chamber reaches the desired temperature more reliably than if there were no air space.

The insulated sample chamber also includes integrated circuit chip 52. The chip contains a sample chamber identification code that is unique to the the particular insulated sample chamber. This sample identification is used during the operation of the device as described below. There is also a connector 54 and cable 56 which allow the insulated sample chamber to be disconnected from the remainder of the instrument 60.

Instrument 60 is also shown in FIG. 1. Instrument 60 contains a microprocessor (not shown) for controlling the heater 12 and for receiving and processing information from heater 12 and temperature sensor 14.

As noted, in preferred embodiments, the total weight of the sample is determined by weighing the sample. Thus, there can be provided balance 40 which communicates with instrument 60 and thereafter the microprocessor by way of cable 42.

Instrument 60 also includes digital readout 62. This readout can display various information during the use of the instrument such as the sample chamber number, the weight of the chamber, the temperature of the chamber and any error messages. Most importantly, when the determination is complete, the snow quality is displayed.

The face of the instrument also includes various push buttons and LED indicators generally indicated by 64. These indicators and buttons are used in the operation of the instrument as described below.

As noted previously, the sample chamber 10 is comprised of a triangular metal cup surrounded by insulating material 22 for thermal preservation of the sample. The thickness and type of insulation is designed in preferred embodiments to limit the transfer of heat to the sample to less than 10 cal/min where the sample is at 0° C. and the insulated sample chamber is in a room temperature environment. About 4 cm of polyurethane foam has been found to be satisfactory.

Attached to the cup is an electrical resistance heater 12 and a solid state temperature sensor 14 (PTAT—Proportional To Absolute Temperature). The electrical heater 12 utilizes a four wire hookup arrangement to accurately measure the amount of heat input into the sample during snow quality determination. Two leads to the heater provide for the delivery of current to the resistance heater while the other two leads allow accurate measurement of the voltage across the heater without measuring the resistance in the leads themselves. Thus the voltage and current to the heater can be accurately measured which, in turn, permits the accurate measurement of the heat that is put into the chamber 10.

The sample chamber also contains a 16 bit digital identification code which is unique to each insulated sample chamber. Since each chamber is unique in that the temperature sensors are not identical and the heat capacity associated with the sample cup, temperature sensor, heater, and overall sample chamber construction are different, an electronic identification code, unique to each chamber, allows these differences to be calibrated out. The electronic identification code allows the microprocessor based instrument to store in its memory each chamber and its associated calibration parameters such that chamber to chamber differences are eliminated from the measurement analysis.

Figure 2:
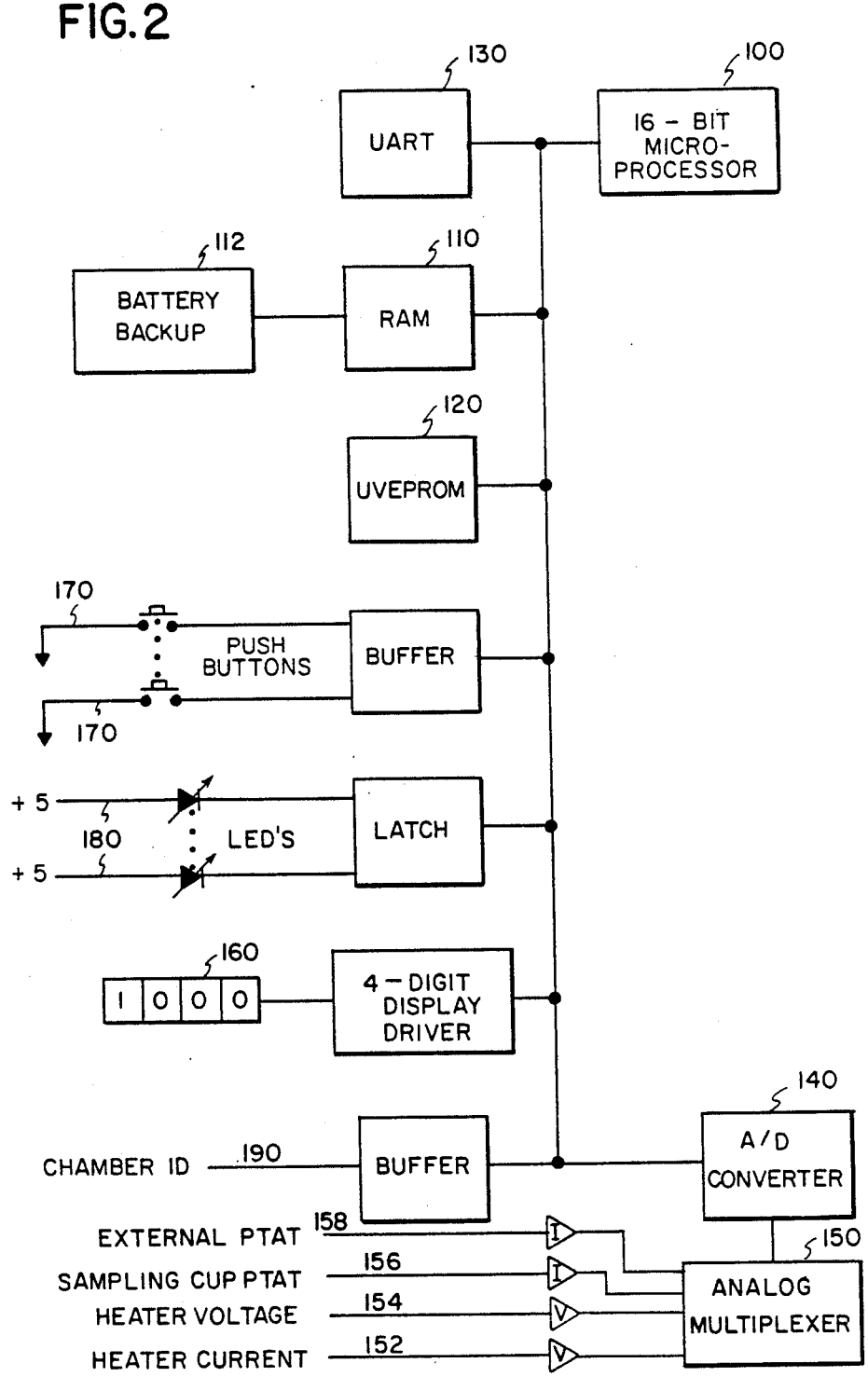
FIG. 2 is a schematic representation of the electronics that are useful in the apparatus of the invention.

The electrical block diagram for the instrument 60 is shown in FIG. 2. The microprocessor based instrument uses a commercially available 16 bit microprocessor 100 having battery backed-up RAM 110, 112, for maintenance of chamber calibration parameters, and a UV EPROM 120 for the permanent maintenance of the program code which operates the instrument. A single RS232-C compatible UART 130 is included in order to communicate with a laboratory balance for weighting the initial and final sample chamber weights, which allows determination of the sample weight. A single analog to digital converter 140, and an associated analog multiplexer 150, allows digitizing of the analog signals associated with the measurements of current through the heater 152, voltage across the heater 154, temperature of the sample cup 156 and the external temperature probe 158, which is used for determination of the boiling point temperature of water at the elevation at which the instrument is calibrated. The microprocessor has peripheral input and output circuitry for driving a 4 digit, 7 segment LED display 160, for sensing the state of push buttons 170 which are part of the user interface to the instrument, for driving LED's 180, which are internal to each push button and part of the user interface and for obtaining the identification code which is associated with each chamber from the chamber identification buffer 190.

The four process measurement signals are preconditioned and amplified using a current amplifier for the two temperature sensors, a voltage divider and amplifier for the voltage across the heater, and a current sense resistor and voltage amplifier for the current flow through the heater.

The instrument is calibrated using a known electrical source having a known current and voltage. Each insulated sample chamber is then calibrated with the instrument by weighing the insulated sample chamber and calibrating the temperature sensor with ice water and boiling water. This information, along with the sample identification number of the insulated sample chamber is then stored in the battery backed up RAM for later use.

Before use, the insulated sample chamber is preconditioned. Crushed ice is prepared and stored in a freezer. A sample of the crushed ice is mixed with water and placed in the sample chamber for at least 10 minutes. This conditions the sample chamber to 0° C. Confirmation of the proper operation of the insulated sample chamber-instrument combination can then be accomplished using dry crushed ice in the sample chamber. The ice percent should be 100%.

The snow quality of a snow sample is determined by first conditioning the insulated sample chamber as noted above to 0° C. The sample chamber is emptied and the snow sample is placed in the chamber and the cover placed in position. Within about one hour, the insulated sample chamber is placed on the balance and connected to the instrument. Pressing of the "initial weight" button on the face of the instrument initiates the determination. The initial weight of the filled insulated sample chamber is recorded by the instrument. Heating begins, confirmed by the illumination of the "heat" LED, and when the sample chamber reaches about 10° C., heating is terminated. The 10° C. final temperature was selected to insure that if any ice were present in the sample, it would all be melted. From the temperature profile during heating and the amount of heat put into the sample, the weight of the ice in the sample is determined. The sample chamber is then emptied and the weight again measured after the "final weight" button is pushed. The difference between the initial and final weight gives the instrument the total weight. With this information and the heating profile, the instrument calculates and displays the snow quality.

The invention has been described in detail with particular reference to preferred embodiments thereof, but it will be understood that variations and modifications can be effected within the spirit and scope of the invention.

We claim:

1. An apparatus for measuring the ice content of snow, said apparatus comprising:
    (a) an insulated sample chamber for receiving a sample of said snow, said sample chamber including:
        (i) means for heating said chamber and
        (ii) means for measuring the temperature of said chamber; and
    (b) computing means detachably connected to said sample chamber including
        (i) means for controlling said means for heating and for measuring the amount of heat supplied to said chamber;
        (ii) means for monitoring said means for measuring temperature; and
        (iii) means for calculating the ice content of said sample from the heat supplied to said chamber and its temperature.

2. An apparatus according to claim 1 wherein said sample chamber is triangular in shape.

3. An apparatus according to claim 1 wherein said insulated sample chamber is insulated with insulating material that does not contact said sample chamber.

4. An apparatus according to claim 1 wherein said insulated sample chamber includes means for uniquely identifying said chamber to said computing means.

* * * * *